United States Patent

Nuñez et al.

(10) Patent No.: US 6,534,665 B1
(45) Date of Patent: Mar. 18, 2003

(54) SINGLE-CARBON BRIDGES BYS CYCLOPENTADIENYL COMPOUNDS AND METALLOCENE COMPLEXES THEREOF

(75) Inventors: Maria Francisca Martinez Nuñez, Madrid (ES); Antonio Muñoz-Escalona LaFuente, Madrid (ES); Begoña Peña Garcia, Madrid (ES); Pilar LaFuente Cañas, Madrid (ES)

(73) Assignee: Repsol Quimica S.A., Madrid (ES)

( * ) Notice: Subject to any disclaimer, the term of this patent is extended or adjusted under 35 U.S.C. 154(b) by 0 days.

(21) Appl. No.: 09/427,522

(22) Filed: Oct. 26, 1999

(51) Int. Cl.$^7$ .................................................. C07F 7/08
(52) U.S. Cl. ................... 556/7; 556/9; 556/11; 556/12; 556/27; 556/52; 556/53; 556/112; 556/113; 556/413; 556/402; 556/428; 556/489; 585/26; 585/27
(58) Field of Search .............. 552/7, 9, 11, 12, 552/27, 52, 53, 42, 43, 413, 402, 428, 489; 585/22, 27

(56) References Cited

FOREIGN PATENT DOCUMENTS

| EP | 0 351 392 A2 | 1/1990 |
| EP | 0 722 949 A2 | 7/1996 |
| EP | 0 751 143 A2 | 1/1997 |
| EP | 0 839 836 A1 | 5/1998 |
| EP | 0 953 581 A1 | 11/1999 |

OTHER PUBLICATIONS

Kesti, M.R., et al., "Homogenous Ziegler–Natta Polymerization of Functionalized Monomers Catalyzed by Cationic Group IV Metallocenes," *J. Am. Chem. Soc.*, vol. 114, pp. 9679–9680 (1992).

Nugent, W.A., et al., "Zirconium–Mediated Ring Construction from Dienes: Remarkable Effect of Ligands on Stereochemistry," *J. Am. Chem. Soc.*, vol. 111, pp. 6435–6437 (1989).

Smith, J.A., et al., "Molecular Structure and Proton Magnetic Resonance Spectra of Methylene—and Ethylene–Bridged Dicyclopentadienyltitanium Compounds,", *Journal of Organometallic Chemistry*, vol. 173, pp. 175–185 (1979).

Wilkinson, G., et al., "Bis–Cyclopentadienyl Derivatives of Some Transition Elements,"*J. Am. Chem. Soc.*, vol. 75, pp. 1011–1012 (1953).

Yasuda, H., et al., "Rare earth metal initiated polymerizations of polar and nonpolar monomers to give high molecular weight polymers with extremely narrow molecular weight distribution," *Macromol. Chem. Phys.*, vol. 196, pp, 2417–2441 (1995).

*Primary Examiner*—Paul F. Shaver
(74) *Attorney, Agent, or Firm*—Ladas & Parry

(57) ABSTRACT

The present invention relates to metallocenes, wherein the two cyclopentadienyl rings are connected to each other by a single carbon atom characterized by the following general formula III

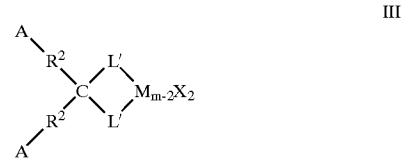

where each A, equal to or different from each other, is selected from the group consisting of: hydrogen, $OR^3$, $NRR^4$, or $SR^5$; and to compounds of formula IV

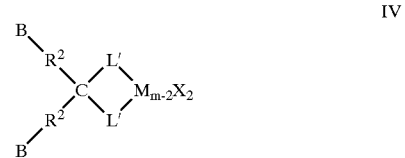

wherein each B, equal to or different from each other, is selected from the group consisting of: OH, NRH or SH, obtained by hydrolizing the corresponding oxygen, nitrogen or sulfur containing groups from compounds of formula III. These compounds are used as active catalyst components in the polymerization of olefins.

24 Claims, No Drawings

SINGLE-CARBON BRIDGES BYS CYCLOPENTADIENYL COMPOUNDS AND METALLOCENE COMPLEXES THEREOF

The present inventions relates to a new process for synthesizing single carbon bridge bis cyclopentadienyl compounds and metal complexes obtained therefrom. And to the use of these complexes for polymerization and copolymerization of olefins.

The metallocene compounds field has experimented a big development since the first syntheses of these compounds in the fifties (G. Wilkinson et al., *J. Am. Chem. Soc.,* (1953), 75, 1011). This development is basically due to the large increase in the number of applications wherein these compounds are used. So, they can be used as catalysts of hydrogenation, epoxidation, double bond isomerization, ketones reduction, aldolic reaction, synthesis of different substituted olefins, etc., but their largest use is as catalyst components for olefin polymerization, as they can be activated for this use by alumoxanes or other non-coordinative anion precursors (for example boron compounds). In this field metallocenes of group 4 (Ti, Zr, Hf, in particular have been developed, but also metallocenes of groups 3, 5 and 6. Metallocenes have been prepared for working in very different conditions (solution, suspension, mass, gas phase, high pressure and temperature processes, etc.). They have been used for polymerizing and copolymerizing simple I-olefins, basically ethylene and propylene, but also more complex olefins (cycloolefins, diolefins and also olefins with polar groups (see for example W. A. Nugent et al., *J. Am. Chem. Soc.* (1989), 111, 6435; R. M. Waymouth et al., *J. Am. Chem. Soc.* (1992), 114, 9679; H. Yasuda et al., *Macromol. Chem. Phys,* (1995), 196,2417).

For adapting to the different needs of each application, very different metallocenes were synthesized, basically differing by the different substitutions on the cyclopentadienyl rings of the complex, as it is possible to influence in this way, both sterically and electronically, the reactivity of the active center. A specially relevant development was the introduction of at least one bridge connecting the two cyclopentadienyl rings (H. H Britzinger et al., *J. Organomet. Chem.,* (1979), 173, 6270), since it determines the reactivity of the metallocene conditioning its steric nature in two ways: (1) influencing the monomer greater or smaller accessibility to the active center as the bridge largerly determines the angle spread between the cyclopentadienyl rings and (2) preventing the free rotation of the rings and, therefore, determining the symmetry of the whole molecule. On the other hand the bridge can also influence the electronic nature of the metallocene. In this way it has been obtained a better stability of certain metallocenes, a greater or smaller discrimination of the monomers that are incorporated into the polymer because of their size and the possibility of obtaining stereoregular I-olefin polymers (isotactic, syndiotactic, hemiiostactic).

It is known hat in order to obtain specific polymer structures, the use of a single-carbon bridge is preferred (e.g. EP A 351 392). A common process for obtaining this type of bridged ligands comprises reacting a ketone with a cyclopentadienyl in the presence of a strong base, then the obtained fulvene is reacted with another cyclopentadienyl compound again in the presence of a base. Generally these procedure requires a purification of the fulvene or optionally the use of a commercially available one.

Particularly for industrial uses, a one-step process is preferred to a two-step process. A one-step process is developed, for example, in EP 751 143, wherein one or two cyclopentadienyl compounds, at least one being a substituted cyclopentadienyl are reacted with a carbonyl compound in the presence of a base and a phase transfer catalyst; the preferred bases are hydroxides of elements belonging to groups 1, 2 or 13 of the periodic table; in the examples sodium hydroxide is used. Another one-step process is described in EP 722 949. It relates to a process for preparing bis-cyclopentadienyl compounds bridged by a single carbon atom. The compound is prepared by reacting a carbonyl compound with a cyclopentadienyl compound in the presence of a base and of an oxygen-containing solvent having an atomic ratio carbon/oxygen not higher than 3.

These one-step processes make use of strong bases such as sodium or potassium hydroxide; therefore they are not adequate for synthesizing bridged bis cyclopentadienyl compounds wherein the bridge is functionalized with hydrolizable groups. On the other hand, bridged bis cyclopentadienyl compounds having these groups, such as for example trialkyl sililoxy group, bonded to the bridge can be useful to obtain complexes that can be, for example, easily supported on a heterogeneous carrier (see for example EP 839 836). Therefore it could be desirable a new process that permits an easy and one-step synthesis of this kind of compounds.

An object of the present invention is a new process for synthesizing single-carbon bridged bis cyclopentadienyl compounds wherein the bridge contains a hydrolizable group.

A further object of the present invention is a new class of single-carbon bridged bis cyclopentadienyl compounds substituted on the bridge with a hydrolizable group, and the metallocene obtained by the use of these ligands.

Another further object of the present invention is a new class of single carbon bridged metallocenes obtained by hydrolisis of the functional group on the bridge.

Another still further object of the present invention is the use of the previosly described metallocenes for polymerization and copolymerization of olefins.

The present invention relates to bis cyclopentadienyl compounds, wherein the two cyclopentadienyl rings are connected to each other by a single carbon atom characterized by the following general formula I

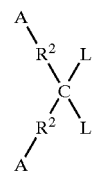

I wherein each L, equal to or different from each other, is selected from the group consisting of:

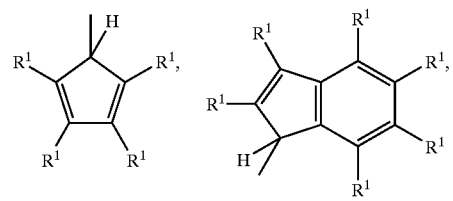

-continued

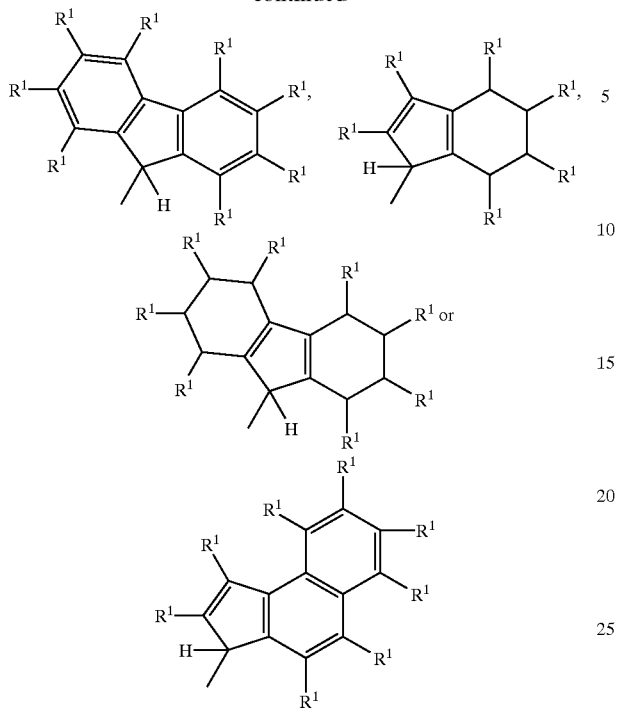

wherein
each $R^1$ equal to or different from each other is selected from the group consisting of hydrogen, a monovalent aliphatic or aromatic hydrocarbon group, optionally containing heteroatoms of group 14 to 16 of the periodic table of the elements and boron; optionally two $R^1$ form an aromatic or aliphatic ring; preferably $R^1$ is selected from the group consisting of: hydrogen, $C_1$–$C_{20}$ alkyl; $C_3$–$C_{20}$ cycloalkyl; $C_6$–$C_{20}$ aryl; $C_2$–$C_{20}$ alkenyl; $C_7$–$C_{20}$ arylalkyl; $C_7$–$C_{20}$ alkylaryl; $C_3$–$C_{20}$ arylalkenyl; $CH_8$–$C_{20}$ alkenylaryl, linear or branched, optionally substituted by $BR_2$, $OR$, $SiR_3$, $NR_2$;

wherein each R is independently selected from the group consisting of $C_1$–$C_{20}$ alkyl, $C_3$–$C_{20}$ cycloalkyl, $C_6$–$C_{20}$ aryl, $C_2$–$C_{20}$ akenyl, $C_7$–$C_{20}$ arylalkyl, $C_7$–$C_{20}$ alkaryl, $C_8$–$C_{20}$ arylalkenyl, $C_8$–$C_{20}$ alkenylaryl linear or branched; two or more R can also form an aliphatic or aromatic ring; preferably R is selected from the group consisting of: butyl, propyl, ethyl, methyl;

each $R^2$, equal to or different from each other, is selected from the group consisting of: $C_1$–$C_{20}$ alkylidene, $C_3$–$C_{20}$ cycloalkylidene, $C_2$–$C_{20}$ alkenylidene, $C_6$–$C_{20}$ arylidene, $C_7$–$C_{20}$ alkylarylidene, $C_7$–$C_{20}$ arylalkylidene, $C_8$–$C_{20}$ arylalkenylidene, $C_8$–$C_{20}$ alkenylarylidene, linear or branched, optionally containing heteroatoms of group 14 to 16 of the periodic table of the elements or boron; one $R^2$ is optionally absent; in this case A is directly bonded to C and is preferably hydrogen; preferably $R^2$ is selected from the group comprising: butylidene, propylidene, ethylidene, methylidene;

each A, equal to or different from each other, is selected from the group consisting of: hydrogen, $OR^3$, $NRR^4$, or $SR^5$ wherein
each $R^3$ is independently selected from the group consisting of: R, $SiR_3$, $SO_2R$, $CR_2OR$; $CR_2SR$, or any other group used as protective group of alcohols in organic synthesis;
each $R^4$ is independently selected from the group consisting of: R, $SiR_3$, $SO_2R$, or any other group used as protective group of amines in organic synthesis;
each $R^5$ is independently selected from the group consisting of: R, $SiR_3$, $CR_2OR$; $CR_2SR$, or any other group used as protective group of thiols in organic synthesis;
wherein R is independently selected from the group consisting of $C_1$–$C_{20}$ alkyl, $C_3$–$C_{20}$ cycloalkyl, $C_6$–$C_{20}$ aryl, $C_2$–$C_{20}$ alkenyl, $C_7$–$C_{20}$ arylalkyl, $C_7$–$C_{20}$ alkylaryl, $C_8$–$C_{20}$ arylalkenyl, $C_8$–$C_{20}$ alkenylaryl linear or branched; optionally two R form a aliphatic or
aromatic ring;
with the proviso that at least one A is not hydrogen.

Preferably A is selected from the group consisting of: hydrogen or $OSiR_3$ non limitative examples of compounds of general formula I are:
1-trimethylsiloxy-4,4-bis(cyclopentadienyl)pentane;
1-trimethylsiloxy-4,4-bis(indenyl)pentane;
1-trimethylsiloxy-4,4-bis(fluorenyl)pentane;
1-trimethylsiloxy-4,4-bis(tetrahydroindenyl)pentane;
1-trimethylsiloxy-4,4-bis(octahydrofluorenyl)pentane;
1,5-bis-trimethylsiloxy-4,4-bis(cyclopentadienyl)pentane;
1,5-bis-trimethylsiloxy-4,4-bis(indenyl)pentane;
1,5-bis-trimethylsiloxy-4,4-bis(fluorenyl)pentane;
1,5-bis-trimethylsiloxy-4,4-bis(tetrahydroindenyl)pentane;
1,5-bis-trimethylsiloxy-4,4-bis(octabydrofluorenyl)pentane;
1-trimethylsiloxy-4-cyclopentadienyl-4-indenyl-pentane;
1-trimethylsiloxy-4-cyclopentadienyl-4-fluorenyl-pentane;
1-trimethylsiloxy-4-cyclopentadienyl-4-tetrahydroindenyl-pentane;
1-trimethylsiloxy-4-cyclopentadienyl-4-octahydrofluorenyl-pentane;
1-trimethylsiloxy-3,3-bis(cyclopentadienyl)pentane;
1-trimethylsiloxy-3,3-bis(indenyl)pentane;
1-trimethylsiloxy-3,3-bis(fluorenyl)pentane;
1-trimethylsiloxy-3,3-bis(tetrahydroindenyl)pentane;
1-trimethylsiloxy-3,3-bis(octahydrofluorenyl)pentane;
1,5-bis-trimethylsiloxy-3,3-bis(cyclopentadienyl)pentane;
1,5-bis-trimethylsiloxy-3,3-bis(indenyl)pentane;
1,5-bis-trimethylsiloxy-3,3-bis(fluorenyl)pentane;
1,5-bis-trimethylsiloxy-3,3-bis(tetrahydroindenyl)pentane;
1,5-bis-trimethylsiloxy-3,3-bis(octahydrofluorenylpentane;
1-trimethylsiloxy-3-cyclopentadienyl-3-indenyl-pentane;
1-trimethylsiloxy-3-cyclopentadienyl-3-fluorenyl-pentane;
1-trimethylsiloxy-3-cyclopentadienyl-3-tetrahydroindenyl-pentane;
1-trimethylsiloxy-3-cyclopentadienyl-3octahydrofluorenyl-pentane;
1-triethylsiloxy-4,4-bis(cyclopentadienyl)pentane;
1-triethylsiloxy-4,4-bis(indenyl)pentane;
1-triethylsiloxy-4,4-bis(fluorenyl)pentane;
1-triethylsiloxy-4,4-bis(tetrahydroindenyl)pentane;
1-triethylsiloxy-4,4-bis(octahydrofluorenyl)pentane;
1,5-bis-triethylsiloxy-4,4-bis(cyclopentadienyl)pentane;
1,5-bis-triethylsiloxy-4,4-bis(indenyl)pentane;
1,5-bis-triethylsifoxy-4,4-bis(fluorenyl)pentane;
1,5-bis-triethylsiloxy-4,4-bis(tetrahydroindenyl)pentane,
1,5-bis-triethylsiloxy-4,4-bis(octahydrofluorenyl)pentane;
1-triethylsiloxy-4-cyclopentadienyl-4-indenyl-pentane;
1-triethylsiloxy-4-cyclopentadienyl-4-fluorenyl-pentane;
1-triethylsiloxy-4-cyclopentadienyl-4-tetrahydroindenyl-pentane;

1-triethylsiloxy-4-cyclopentadienyl-4-octahydrofluorenyl-pentane;
1-triethylsiloxy-3,3-bis(cyclopentadienyl)pentane;
1-triethylsiloxy-3,3-bis(indenyl)pentane;
1-triethylsiloxy-3,3-bis(fluorenyl)pentane;
1-triethylsiloxy-3,3-bis(tetrahydroindenyl)pentane,
1-triethylsiloxy-3,3-bis(octahydrofluorenyl)pentane;
1,5-bis-triethylsiloxy-3,3-bis(cyclopentadienyl)pentane;
1,5-bis-triethylsiloxy-3,3-bis(indenyl)pentane;
1,5-bis-triethylsiloxy-3,3-bis(fluorenyl)pentane;
1,5-bis-triethylsiloxy-3,3-bis(tetrahydroindenyl)pentane;
1,5-bis-trimethylsiloxy-3,3-bis(octahydrofluorenyl)pentane;
1-triethylsiloxy-3-cyclopentadienyl-3-indenyl-pentane;
1-triethylsiloxy-3-cyclopentadienyl-3-fluorenyl-pentane;
1-triethylsiloxy-3-cyclopentadienyl-3-tetaydroindenyl-pentane;
1-triethylsiloxy-3-cyclopentadienyl-3-octahydrofluorenyl-pentane;
1-triphenylsiloxy-4,4-bis(cyclopentadienyl)pentane;
1-triphenylsiloxy-4,4-bis(indenyl)pentane;
1-triphenylsiloxy-4,4-bis(fluorenyl)pentane;
1-triphenylsiloxy-4,4-bis(tetrahydroindenyl)pentane;
1-triphenylsiloxy-4,4-bis(octahydrofluorenyl)pentane;
1,5-bis-triphenylsiloxy-4,4-bis(cyclopentadienyl)pentene;
1,5-bis-triphenylsiloxy-4,4-bis(indenyl)pentane;
1,5-bis-triphenylsiloxy-4,4-bis(fluorenyl)pentane;
1,5-bis-triphenylsiloxy-4,4-bis(tetrahydroindenyl)pentane;
1,5-bis-triphenylsiloxy-4,4-bis(octahydrofluorenyl)pentane;
1-triphenylsiloxy-4-cyclopentadienyl-4indenyl-pentane,
1-triphenylsiloxy-4-cyclopentadienyl-4-fluorenyl-pentane;
1-triphenylsiloxy-4-cyclopentadienyl-4-tetrahydroindenyl-pentane;
1-triphenylsiloxy-4-cyclopentadienyl-4-octahydrofluorenyl-pentane;
1-triphenylsiloxy-3,3-bis(cyclopentadienyl)pentane;
1-triphenylsiloxy-3,3-bis(indenyl)pentane;
1-triphenylsiloxy-3,3-bis(fluorenyl)pentane;
1-triphenylsiloxy-3,3-bis(tetrahydroindenyl)pentane;
1-triphenylsiloxy-3,3-bis(octahydrofluorenyl)pentane;
1,5-bis-triphenylsiloxy-3,3-bis(cyclopentadienyl)pentane;
1,5-bis-triphenylsiloxy-3,3-bis(indenyl)pentane;
1,5-bis-triphenylsiloxy-3,3-bis(fluorenyl)pentane;
1,5-bis-triphenylsiloxy-3,3-bis(tetrahydroindenyl)pentane;
1,5-bis-tiphenylsiloxy-3,3-bis(octahydrofluorenyl)pentane,
1-triphenylsiloxy-3-cyclopentadienyl-3-indenyl-pentane;
1-triphenylsiloxy-3-cyclopentadienyl-3-fluorenyl-pentane;
1-triphenylsiloxy-3-cyclopentadienyl-3-tetrahydroindenyl-pentane;
1-triphenylsiloxy-3-cyclopentadienyl-3-octahydrofluorenyl-pentane;

Compounds according to the present invention are synthesized according to a one-step process comprising: contacting a compound (LH) selected from the group consisting of:

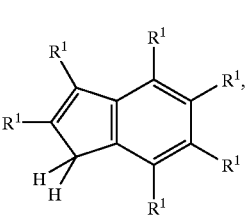

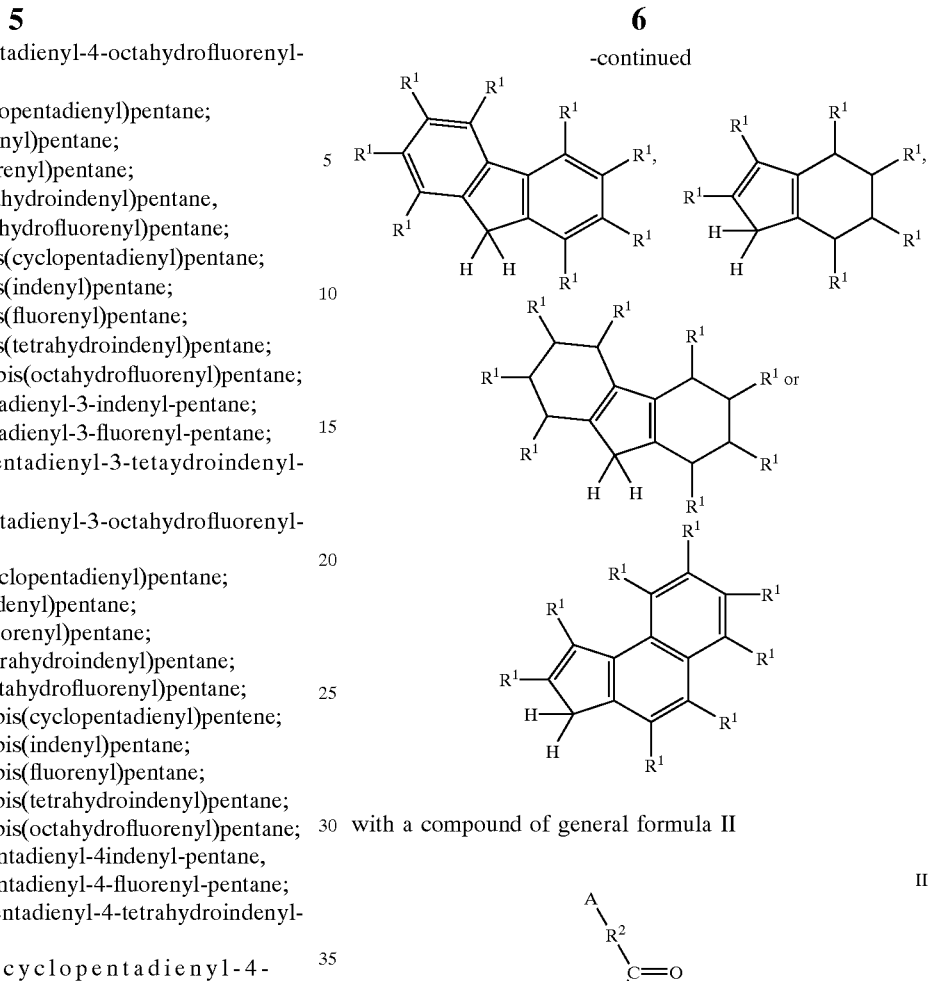

with a compound of general formula II

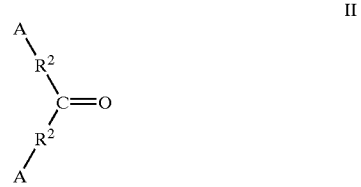

in the presence of a metallating compound selected from the group consisting of: organolithium compounds, organosodium compounds, organopotassium compounds, organomagnesium, sodium hydride, potassium hydride, lithium, sodium, or potassium; preferably lithium alkyl, sodium alkyl potassium alkyl; more preferably butyllithium; increasing the temperature and recovering the product.

Preferably the compound LH is put in contact with the metallating compound and then the compound of formula II is added.

Preferably for one mole of compound of formula II two moles of LH and two moles of the metallating compound are used.

Non limitative examples of compounds of general formula II are;
1-trimethylsiloxy-pentane-2-one,
1-triethylsiloxy-pentane-3-one;
1-triethylsiloxy-pentane-4-one;
1,5-bis-triethylsiloxy-pentane-3-one;
1-trimethylsiloxy-hexane-5-one;
1-trimethylsiloxy-hexane-4-one;
1-trimethylsiloxy-hexane-3-one;
1-trimethylsiloxy-hexane-2-one;
1,6-bis-trimethylsiloxy-hexane-3-one;
1-trimethylsiloxy-heptane-6-one;
1-trimethylsiloxy-heptane-5-one;
1-trimethylsiloxy-heptane-4-one;
1-trimethylsiloxy-heptane-4-one;

1-trimethylsiloxy-heptane-2-one;
1,7-bis-trimethylsiloxy-heptane-4-one;
1-triethylsiloxy-pentane-2-one;
1-triethylsiloxy-pentane-3-one;
1-triethylsiloxy-pentane-4-one;
1,5-bis-triethylsiloxy-pentane-3-one;
1-triethylsiloxy-hexane-5-one;
1-triethylsiloxy-hexane-4-one;
1-triethylsiloxy-hexane-3-one;
1-triethylsiloxy-hexane-2-one;
1,6-bis-triethylsiloxy-hexane-3-one;
1-triethylsiloxy-heptane-6-one;
1-triethylsiloxy-heptane-5-one;
1-triethylsiloxy-heptane-4-one;
1-triethylsiloxy-heptane-3-one;
1-triethylsiloxy-heptane-2-one;
1,7-bis-triethylsiloxy-heptane-4-one;
1-triphenylsiloxy-pentane-2-one;
1-triphenylsiloxy-pentane-3-one;
1-triphenylsiloxy-pentane-4-one;
1,5-bis-1-triphenylsiloxy-pentane-3-one:
1-triphenylsiloxy-hexane-5-one;
1-triphenylsiloxy-hexane-4-one;
1-triphenylsiloxy-hexane-3-one;
1-triphenylsiloxy-hexane-2-one;
1,6-bis-1-triphenylsiloxy-hexane-3-one;
1-triphenylsiloxy-heptane-6-one;
1-triphenylsiloxy-heptane-5-one;
1-triphenylsiloxy-heptane-4-one;
1-triphenylsiloxy-heptane-3-one;
1-triphenylsiloxy-heptane-2-one;
1,7-bis-1-triphenylsiloxy-heptane-4-one;

The process is realized in a temperature range between −100 and 150° C., preferably between −78 and 90° C., or at the reflux temperature of the used solvents system, it is also possible to vary the temperature during the process. Any kind of solvent compatible with the reactants is used, preferably an aliphatic hydrocarbon, an aromatic hydrocarbon, or an ether, for instance: hexane, toluene, tetahydrofurane (THF) or ethyl ether. The process is preferably carried out under inert atmosphere of, for example nitrogen or argon, and with anhydrous solvents. The skilled man can select the appropriate reaction conditions on the basis of his knowledge and the reactants used.

In a particular embodiment wherein two L groups are different, the single carbon bridged bis cyclopentadienyl compound, object of the present invention, is obtained by a one-pot process comprising: contacting a compound (LH) selected from the group consisting of:

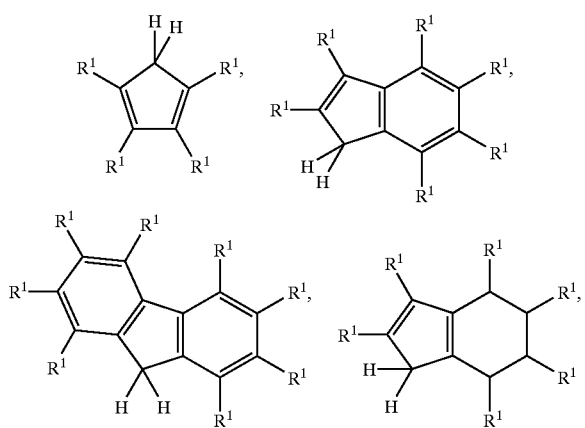

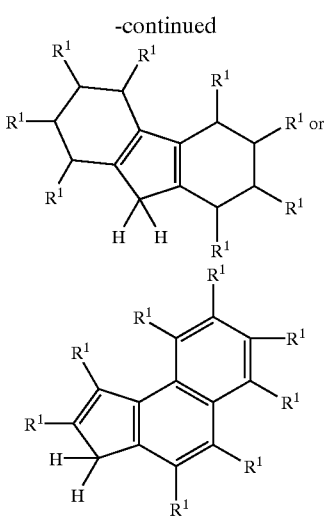

with a metallating compound selected from the group consisting of: organolithium compounds, organosodium compounds, organopotassium compounds, organomagnesium, sodium hydride, potassium hydride, lithium, sodium, or potassium; preferably lithium alkyl, sodium alkyl, potassium alkyl; more preferably butyllithium;

with a compound of general formula II

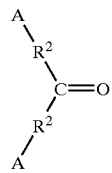

adding a second compound LH different from the first one;

adding a second amount of metallating compound as above defined;

increasing the temperature and recovering the product.

Preferably the compound LH is contacted with the compound of formula II in the presence of a metallating compound, then a second compound LH and the metallating compound are mixed; the mixture is then introduced to the reaction mixture.

Preferably for one mole of compound of formula II one mole of the first LH compound, one mole of the second one and two moles of a metallating compounds are used. More preferably an quimolar mixture of LH and metallating agent is put in contact with a compound of formula II, then an equimolar mixture of an LH compound different from the first one and a metallating agent is added to the reaction product.

The skilled man can select on the basis of his knowledge the appropriate temperatures of the first and the second phase that depends from the cyclopentadienyl compounds used. Usually the first phase is performed at a temperature range from −78° C. to room temperature and the second phase at a temperature range from −78° C. to the boiling point of the solvent.

The single-carbon bridged cyclopentadienyl compounds object of the present invention are used for synthesizing metallocene complexes of general formula III

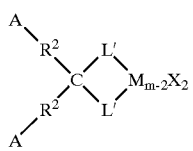

Wherein:

Each L' is independently a cyclopentadienyl compound and forms with the metal a $\eta^5$ complex, it is selected from the group consisting of:

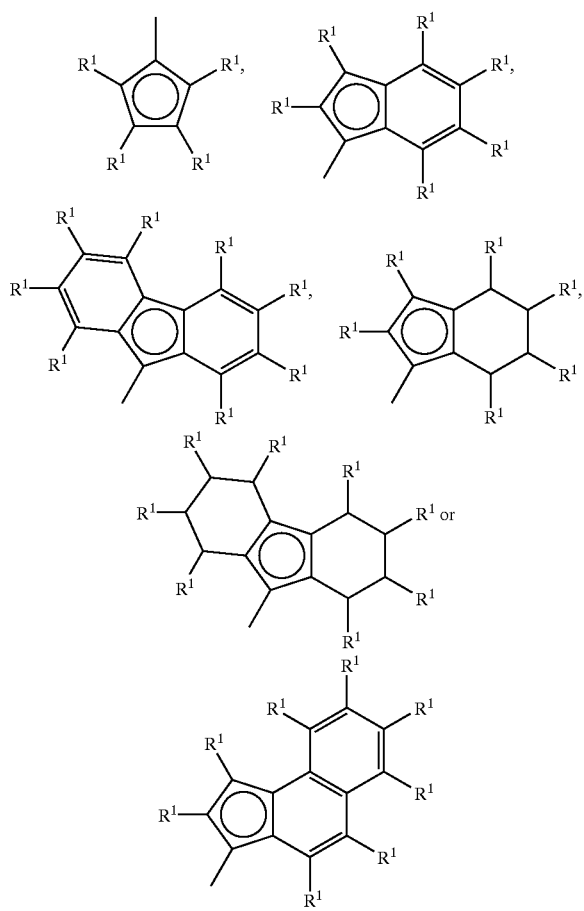

M is a tranition metal of groups 3–6 of the periodic table; preferably it is selected from the group consisting of zirconium, titanium or hafnium;

m is a number coinciding with the oxidation state of the transition metal;

Each X, equal to or different from each other, is selected from the group comprising, halogen, hydrogen, OR, $N(R)_2$, $C_1$–$C_{20}$ alkyl or $C_6$–$C_{20}$ aryl; preferably it is halogen.

Examples of metallocenes of formula III are:
(1-trimethylsiloxy-4,4-bis(cyclopentadienyl)pentane) zirconium dichloride;
(1-trimethylsiloxy-4,4-bis(indenyl)pentane)zirconium dichloride;
(1-trimethylsiloxy-4,4-bis(fluoreny)pentane)zirconium dichloride;
(1-trimethylsiloxy-4,4-bis(tetrahydroindenyl)pentane) zirconium dichloride;
(1-trimethylsiloxy-4,4-bis(octahydrofluorenyl)pentane) zirconium dichloride;
(1,5-bis-trimethylsiloxy-4,4-bis(cyclopentadienyl)pentane) zirconium dichloride;
(1,5-bis-trimethylsiloxy-4,4-bis(indenyl)pentane)zirconium dichloride;
(1,5-bis-trimethylsiloxy-4,4-bis(fluorenyl)pentane) zirconium dichloride;
(1,5-bis-trimethylsiloxy-4,4-bis(tetrahydroindenyl)pentane) zirconium dichloride;
(1,5-bis-trimethylsiloxy-4,4-bis(octahydrofluorenyl) pentane)zirconiurn dichloride;
(1-trimethylsiloxy-4-cyclopentadienyl-4-indenyl-pentane) zirconium dichloride;
(1-trimethylsiloxy-4-cyclopentadienyl-4-fluorenyl-pentane) zirconium dichloride;
(1-trimethylsiloxy-4-cyclopentadienyl-4-tetrahydroindenyl-pentane)zirconium dichloride;
(1-trimethylsiloxy-4-cyclopentadienyl-4-octahydrofluorenyl-pentane)zirconium dichloride;
(1-trimethylsiloxy-3,3-bis(cyclopentadienyl)pentane) zirconium dichloride;
(1-trimethylsiloxy-3,3-bis(indenyl)pentane)zirconium dichloride;
(1-trimethylsiloxy-3,3-bis(fluorenyl)pentane)zirconium dichloride;
(1-trimethylsiloxy-3,3-bis(tetrahydroindenyl)pentane) zirconium dichloride;
(1-trimethylsiloxy-3,3-bis(octahydrofluorenyl)pentane) zirconium dichloride;
(1,5-bis-trimethylsiloxy-3,3-bis(cyclopentadienyl)pentane) zirconium dichloride;
(1,5-bis-trimethylsiloxy-3,3-bis(indenyl)pentane)zirconium dichloride;
(1,5-bis-trimethylsiloxy-3,3-bis(fluorenyl)pentane) zirconium dichloride;
(1,5-bis-trimethylsiloxy-3,3-bis(tetrahydroindenyl)pentane) zirconium dichloride,
(1,5-bis-trimethylsiloxy-3,3-bis(octahydrofluorenyl) pentane)zirconium dichloride;
(1-trimethylsiloxy-3-cyclopentadienyl-3-indenyl-pentana) zirconium dichloride;
(1-trimethylsiloxy-3-cyclopentadienyl-3-fluorenyl-pentane) zirconium dichloride;
(1-trimethylsiloxy-3-cyclopentadienyl-3-tetrahydroindenyl-pentane)zirconium dichloride;
(1-trimethylsiloxy-3-cyclopentadienyl-3-octahydrofluorenyl-pentane)zirconium dichloride;
(1-triethylsiloxy-4,4-bis(cyclopentadienyl)pentane) zirconium dichloride;
(1-triethylsiloxy-4,4-bis(indenyl)pentane)zirconium dichloride;
(1-triethylsiloxy-4,4-bis(fluorenyl)pentane)zirconium dichloride;
(1-triethylsiloxy-4,4-bis(tetrahydroindenyl)pentane) zirconium dichloride;
(1-triethylsiloxy-4,4-bis(octahydrofluorenyl)pentane) zirconium dichloride;

(1,5-bis-triethylsiloxy-4,4-bis(cyclopentadienyl)pentane) zirconium dichloride;
(1,5-bis-triethylsiloxy-4,4-bis(indenyl)pentane)zirconium dichloride;
(1,5-bis-triethylsiloxy-4,4-bis(fluorenyl)pentane)zirconium dichloride;
(1,5-bis-triethylsiloxy-4,4-bis(tetrahydroindenyl)pentane) zirconium dichloride;
(1,5-bis-triethylsiloxy-4,4-bis(octahydrofluorenyl)pentane) zirconium dichloride;
(1-triethylsiloxy-4-cyclopentadienyl-4-indenyl-pentane) zirconium dichloride;
(1-triethylsiloxy-4-cyclopentadienyl-4fluorenyl-pentane) zirconium dichloride;
(1-triethylsiloxy-4-cyclopentadienyl-4-tetrahydroindenyl-pentane)zirconium dichloride;
(1-triethylsiloxy-4-cyclopentadienyl-4-octahydrofluorenyl-pentane)zirconium dichloride;
(1-triethylsiloxy-3,3-bis(cyclopentadienyl)pentane) zirconium dichloride;
(1-triethylsiloxy-3,3-bis(indenyl)pentane)zirconium dichloride;
(1-triethylsiloxy-3,3-bis(fluorenyl)pentane)zirconium dichloride;
(1-triethylsiloxy-3,3-bis(tetrahydroindenyl)pentane) zirconium dichloride;
(1-triethylsiloxy-3,3-bis(octahydrofluorenyl)pentane) zirconium dichloride;
(1,5-bis-triethylsiloxy-3,3-bis(cyclopentadienyl)pentane) zirconium dichloride,
(1,5-bis-triethylsiloxy-3,3-bis(indenyl)pentane)zirconium dichloride;
(1,5-bis-triethylsiloxy-3,3-bis(fluorenyl)pentane)zirconium dichoride;
(1,5-bis-triethylsiloxy-3,3-bis(tetrahydroindenyl)pentane) zirconium dichloride;
(1,5-bis-triethylsiloxy-3,3-bis(octahydrofluorenyl)pentane) zirconium dichloride;
(1-triethylsiloxy-3-cyclopentadienyl-3-indenyl-pentane) zirconium dichloride;
(1-triethylsiloxy-3-cyclopentadienyl-3-fluorenyl-pentane) zirconium dichloride;
(1-triethylsiloxy-3-cyclopentadienyl-3-tetrahydroindenyl-pentane)zirconium dichloride;
(1-triethylsiloxy-3-cyclopentadienyl-3-octahydrofluorenyl) pentane)zirconium dichloride;
(1-triphenylsiloxy-4,4-bis(cyclopentadienyl)pentane) zirconium dichloride;
(1-triphenylsiloxy-4,4-bis(indenyl)pentane)zirconium dichloride;
(1-triphenylsiloxy-4,4-bis(fluorenyl)pentane)zirconium dichloride;
(1-triphenylsiloxy-4,4-bis(tetahydroindenyl)pentane) zirconium dichoride;
(1-triphenylsiloxy-4,4-bis(octahydrofluorenyl)pentane) zirconium dichloride;
(1,5-bis-triphenylsiloxy-4,4-bis(cyclopentadienyl)pentane) zirconium dichloride;
(1,5-bis-triphenylsiloxy-4,4-bis(indenyl)pentane)zirconium dichloride;
(1,5-bis-triphenylsiloxy-4,4-bis(fluorenyl)pentane) zirconium dichloride;
(1,5-bis-triphenylsiloxy-4,4-bis(tetraydroindenyl)pentane) zirconium dichloride;
(1,5-bis-triphenylsiloxy-4,4-bis(octahydrofluorenyl) pentane)zirconium dichloride;
(1-triphenylsiloxy-4-cyclopentadienyl-4-indenyl-pentane) zirconium dichloride;
(1-triphenylsiloxy-4-cyclopentadienyl-4-fluorenyl-pentane) zirconium dichloride;
(1-triphenylsiloxy-4-cyclopentadienyl-4-tetrahydroindenyl-pentane)zirconium dichloride;
(1-triphenylsiloxy-4-cyclopentadienyl-4-octahydrofluorenyl-pentane)zirconium dichloride;
(1-triphenylsiloxy-3,3-bis(cyclopentadienyl)pentane) zirconium dichloride;
(1-triphenylsiloxy-3,3-bis(indenyl)pentane)ziconium dichloride;
(1-triphenylsiloxy-3,3-bis(fluorenyl)pentane)zirconium dichloride;
(1-triphenylsiloxy-3,3-bis(tetrahydroindenyl)pentane) zirconium dichloride;
(1-triphenylsiloxy-3,3-bis(octahydrofluorenyl)pentane) zirconium dichloride;
(1,5-bis-triphenylsiloxy-3,3-bis(cyclopentadienyl)pentane) zirconium dichloride;
(1,5-bis-triphenylsiloxy-3,3-bis(indenyl)pentane)zirconium dichloride;
(1,5-bis-triphenylsiloxy-3,3-bis(fluorenyl)pentane) zirconium dichloride;
(1,5-bis-triphenylsiloxy-3,3-bis(tetrahydroindenyl)pentane) zirconium dichloride;
(1,5-bis-triphenylsiloxy-3,3-bis(octahydrofluorenyl) pentane)zirconium dichloride;
(1-triphenylsiloxy-3-cyclopendienyl-3-indenyl-pentane) zirconium dichloride;
(1-triphenylsiloxy-3-cyclopentadienyl-3-fluorenyl-pentane) zirconium dichloride;
(1-triphenylsiloxy-3-cyclopentadienyl-3-tetrahydroindenyl-pentane)zirconium dichloride;
(1-triphenylsiloxy-3-cyclopentadienyl-3-octahydrofluorenyl-pentane)zirconium dichloride;

The metallocene complexes of general formula III are synthesized according to a process comprising the following steps:

a) reacting a compound of general formula I with two equivalents of a strong base selected from the group consisting of: organolithium compounds, organosodium compounds, organopotassium compounds, organomagnesium, sodium hydride, potassium hydride, lithium, sodium, or potassium; preferably lithium alkyl, sodium alkyl, potassium alkyl; more preferably butyl-lithium;

b) reacting the bimetallated reaction product with one equivalent of a compound of general formula $MX_mE_q$ wherein E is an ether or an amine forming an adduct with M and q is 0, 1, 2, 3 or 4.

With compounds of formula M it is possible to synthesize compounds of general formula IV:

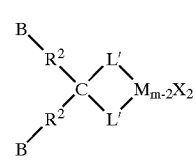

IV wherein each B, equal to or different from each other, is selected from the group consisting of: OH, NRH or SH by hydrolizing the corresponding oxygen, nitrogen or sulfur containing groups.

Examples of such compounds are
(1-hydroxy-4,4-bis(cyclopentadienyl)pentane) zirconium dichloride;
(1-hydroxy-4,4-bis(indenyl)pentane) zirconium dichloride;

(1-hydroxy-4,4-bis(fluorenyl)pentane) zirconium dichloride;
(1-hydroxy-4,4-bis(tetrahydroindenyl)pentane) zirconium dichloride;
(1-hydroxy-4,4-bis(octahydrofluorenyl)pentane) zirconium dichloride;
(1,5-bis-hydroxy-4,4-bis(cyclopentadienyl)pentane) zirconium dichloride;
(1,5-bis-hydroxy-4,4-bis(indenyl)pentane) zirconium dichloride;
(1,5-bis-hydroxy-4,4-bis(fluorenyl)pentane) zirconium dichloride;
(1,5-bis-hydroxy-4,4-bis(tetrahydroindenyl)pentane) zirconium dichloride;
(1,5-bis-hydroxy-4,4-bis(octahydrofluorenyl)pentane) zirconium dichloride;
(1-hydroxy-4-cyclopentadienyl-4-indenyl-pentane) zirconium dichloride,
(1-hydroxy-4-cyclopentadienyl-4-fluorenyl-pentane) zirconium dichloride;
(1-hydroxy-4-cyclopentadienyl-4-tetrahydroindenyl-pentane) zirconium dichloride;
(1-hydroxy-4-cyclopentadienyl-4-octahydrofluorenyl-pentane) zirconium dichloride;
(1-hydroxy-3,3-bis(cyclopentadienyl)pentane) zirconium dichloride;
(1-hydroxy-3,3-bis(indenyl)pentane) zirconium dichloride;
(1-hydroxy-3,3-bis(fluorenyl)pentane) zirconium dichloride;
(1-hydroxy-3,3-bis(tetrahydroindenyl)pentane) zirconium dichloride;
(1-hydroxy-3,3-bis(octahydrofluorenyl)pentane) zirconium dichloride;
(1,5-bis-hydroxy-3,3-bis(cyclopentadienyl)pentane) zirconium dichloride;
(1,5-bis-hydroxy-3,3-bis(indenyl)pentane) zirconium dichloride;
(1,5-bis-hydroxy-3,3-bis(fluorenyl)pentane) zirconium dichloride;
(1,5-bis-hydroxy-3,3-bis(tetrahydroindenyl)pentane) zirconium dichloride;
(1,5-bis-hydroxy-3,3-bis(octahydrofluorenyl)pentane) zirconium dichloride;
(1-hydroxy-3-cyclopentadienyl-3-indenyl-pentane) zirconium dichloride;
(1-hydroxy-3-cyclopentadienyl-3-fluorenyl-pentane) zirconium dichloride;
(1-hydroxy-3-cyclopentadienyl-3-tetrahydroindenyl-pentane) zirconium dichloride;
(1-hydroxy-3-cyclopentadienyl-3-octahydrofluorenyl-pentane) zirconium dichloride;

The skilled man can select reactants and conditions for performing this hydrolization reaction; for example compounds wherein the group A is $OSiR_3$ are hydrolized to form an OH group by using silica gel, or any other chemical reaction with the appropriate reactants that deprotects the funtional group.

The metallocenes of the present invention are particularly adequate as catalyst component for polymerizing olefins, preferably alpha-olefins in combination with a cocatalyst. Illustrative but non-limiting non-limiting examples of co-catalysts are: aluminoxanes (MAO, MMAO, etc.), combinations of alkyl aluminiums (such as trimethylaluminum, triethylaluminium, tributylaluminium, etc.) and boron Lewis acids (such as trifluoroborate, trispentafluorophenylborane, tris[3,5-bis(trifluoromethyl)phenyl]borane, etc.), Lewis acids (dimethylanilium tetrakis(pentafluorophenyl)boron, $HBF_4$, $AgBF_4$, $AgPF_6$, $AgSbF_6$, silver tetrakis[3,5-bis(trifluoromethyl)phenyl]borate sodium tetrakis[3,5-bis(trifluoromethyl)phenyl]borate, etc.).

The catalyst component of the present invention, i.e. the metallocene complex of formula III or IV (preferably when at least a hydrolizable group A in formula III is $OSiR_3$ or when in formula IV at least one B is OH), is especially fit for being supported on a proper inorganic support as described in EP 839 836. As supporting material, any type of inorganic oxides are used, for example inorganic oxides such as: silica, alumina, silica alumina, aluminum phosphates and mixtures thereof, obtaining supported catalysts with contents in transition metals between 0.01 and 4% by weight, preferably between 0.1 and 1%. A particularly preferred support is silica calcined at a temperature between 600° C. and 800° C. and also MAO modified silica.

A process that is fit for preparing supported catalysts according to this invention comprises the following steps:

a) reacting, under anhydrous conditions and inert atmosphere, a solution of at least one metallocene complex of formula III or IV, with a suspension of the supporting material at a temperature between −20° C. and 90° C. The solvent used for this procedure is an aliphatic or aromatic hydrocarbon.

b) filtration and washing with a aliphatic or aromatic hydrocarbon.

Another process that can properly be used comprises the following steps:

a) reacting at least one metallocene complex of formula III or IV with the supporting material by using a solution of the compound to heterogenize;

b) eliminating the solvent through evaporation;

c) warming the solid residue up to a temperature between 25 and 150° C.

Besides, the resulting residue obtained by this process, is optionally subjected to washing and subsequent filtration.

The amount of metallocene of formula III or formula IV which is anchored in these conditions directly depends on the concentration of the reactive groups present in the support. For this reason silica, for example, should preferably have been calcinated at a temperature between 600° C. and 800° C.

A solid catalyst system is obtained by adding to the solid catalyst component a cocatalyst, for example alumoxane, boron compounds or mixtures thereof, at any step of the processes described above. In a particularly advantageous process the cocatalyst, preferably alumoxane, is added to the support, preferably silica, and then the treated support is reacted with the metallocene of formula III or IV according to the process described in patent 98500101.5.

For the polymerization in solution, the cocatalyst is partly premixed with a solution of a metallocene complex according to formula III or IV and is partly added directly to the reaction medium; alternatively, the catalyst is directly added to the polymerization medium, which contains the cocazalyst.

For the polymerization in suspension, the cocatalyst either is previously mixed with the supported solid catalyst or it is added to the polymerization medium before the supported catalyst, or both operations are sequentially realized.

The most proper polymerization procedure changes according to the chosen type of polymerization process (solution, suspension, slurry or gas phase).

The process consists in putting in contact the monomer, or, in certain cases, the monomer and the comonomer, with a catalytic composition according to the present invention that includes at least one metallocene of formulas III or IV, at a proper temperature and pressure.

$C_2$–$C_8$ alpha-olefins, such as ethylene, propylene, 1-butene, 1-hexene, 1-octene, 4-methyl-1-pentene are used as monomer. In case ethylene is used as the monomer, it is polymerized either one or in combination with a comonomer. Preferred comonomers are propylene, butene, hexene, octene or branched ones such as 4-methyl-1-pentene and are used in proportions from 0.1 to 70% by weight of the total of the monomers. In the case of homopolymerization of ethylene the density of the obtained polymers ranges between 0.950 and 0.965 kg/cm$^3$; in the case of copolymerization of ethylene, the density is as low as 0.900 kg/cm$^3$.

In the particular case of the polymerization technique known as suspension process or controlled particle morphology process, the used temperature will be between 30° and 110° C., the same which is typically used in gas phase, while for the solution process the usual temperature will be between 120° and 250° C.

The used pressure changes according to the polymerization technique; it ranges from atmospheric pressure to 350 MPa.

The following examples are described in order to better understand the invention. The materials, the chemical compounds and the conditions used in these examples are illustrative and do not limit the scope of the invention.

EXAMPLES

All air and/or moisture sensitive compounds were manipulated using standard vacuum line, Schlenk and cannula techniques or in a glovebox under a nitrogen atmosphere. All solvents were distilled over sodium and benzophenone and stored under nitrogen, NMR spectra were recorded on a Broker avance DRX 500 spectrometer at 500 MHz.

Example 1

Synthesis of 5-trimethylsiloxypentan-2-one 5-hydroxy-2-pentanone (39.7 g, 0.39 mol) was placed in a three-neck round bottom flask equipped with a bubbler. A few drops of trimethylsilylchloride were added to the flask and then hexamethyldixilazane (31.4 g, 0.20 mol) was dropped via addition funnel over half an hour period. Ammonia evolved vigorously from the reaction and temperature increased. After addition, the mixture was slowly heated until 125° C., Evolution of NH$_3$ ceased after 10 minutes, but heating was maintained at that temperature for one additional hour. The product was distilled at 10 mbar and 61–65° C., yielding a colorless oil (38.0 g, 56% yield). $^1$H NMR (CDCl$_3$): $\Lambda$3.45 (CH$_2$, t, 2H), 2.37 (CH$_2$, t, 2H), 2.02 (CH$_3$, s, 3H), 1.66 (CH$_2$, m, 2H), −0.03 ((CH$_3$)$_3$, s, 9H).

Example 2

Synthesis of 2,2-bis(cyclopentadienyl)-5-trimethylsiloxypentane

Freshly distilled cyclopentadiene (61.5 g, 0.93 mol) was placed in a one liter Schlenk flask and dissolved in dry THF (500 ml). n-BuLi 2.5 M in hexane (372 ml 0.93 mol) was slowly added to this solution at −78° C., yielding a white precipitate. The suspension was left to reach room temperature and then heated to 65° C. for one hour. The reaction mixture is thermostated at 20° C. and a solution of 5-trimethylsiloxypentan-2-one (72.5 g, 0.42 mol) in THF (100 ml) was slowly added. The yellow suspension obtained was heated at reflux for 16 h. The resulting brown suspension was filtered and the solid washed with hexane several times. Solvents were removed under vacuum and the orange oil obtained was distilled at 10$^{-3}$ mbar and 84–89° C., obtaining a yellow oil (20.5 g, 17% yield). $^1$H NMR (CDCl$_3$): $\Lambda$6.40–6.02 (C$_5$H$_5$, 6H), 3.55 (CH$_2$, m, 2H), 2.97, 2.80 and 2.78 (C$_5$H$_5$, 4H), 1.82 (CH$_2$, m, 2H), 1.42 (CH$_2$, m, 2H), 1.40 (CH$_3$, s, 3H), 0.10 ((CH$_3$)$_3$, s, 9H).

Example 3

Synthesis of 2,2-bis(cyclopentadienyl)-5-trimethylsiloxypentane zirconium dichloride The previously distilled ligand (20.2 g, 0.07 mol) was placed in a 500 ml Schlenk flask and dissolved in dry hexane (250 ml). n-BuLi 1.6 M in hexane (87.3 ml 0.14 mol) was dropwise added is solution at 5° C. The resulting white suspension was heated to 75° C. for a 6 h period until the total formation of the dilithium salt was confirmed by NMR. The mixture was left to cool down to room temperature, filtered and dried under vacuum. ZrCl$_4$ (16.28 g, 0.07 mol) was placed in the 500 Schlenk flask and toluene (200 ml) was added, and, at the same time, toluene (200 ml) was added to 2,2-bis(cyclopentadienyl)-5trimethylsiloxypentane dilithium salt. Both suspensions were cooled to −78° C. and the dilithium salt slurry was, via cannula, added to the ZrCl$_4$ one. The resulting off-white suspension was allowed to warm to room temperature and stirred for 16 h. The resulting orange-red suspension was filtered and the cake washed with toluene (100 ml). The solvent was removed under vacuum and the resulting oily solid was repeatedly extracted with hexane, concentrated to 1/10 in volume and cooled to −30° C. to afford yellow crystals of the product (6.8 g, 22% yield). $^1$H NMR (CDCl$_3$): $\Lambda$6.70 (C$_5$H$_4$, d, 4H), 5.82 (C$_5$H$_4$, d, 4), 3.75 (CH$_2$, t, 2H), 2.28 (CH$_2$, m, 2H), 1.83 (CH$_2$, m, 2H), 1.80 (CH$_3$, s, 3H), 0.18 ((CH$_3$)$_3$, s, 9H).

Example 4

Synthesis of 2,2-bis(cyclopentadienyl)-5-hydroxypentane zirconium dichloride

XPO 2407 silica, provided by Grace, (7.2 g) was placed in a 250 ml dark-coloured Schlenk flask and washed with toluene (2×200 ml). Toluene (150 ml) and a solution of 2,2-bis(cyclopentadienyl)-5-trimethylsiloxypentane zirconium dichloride (2.0 g, 0.0045 mol) in toluene (50 ml) were added and the slurry was stirred for 90 h. After this time the mixture was filtered and the solvent removed under vacuum. Affording a yellow solid (0.16 g, 9.5% yield). $^1$H NMR (CDCl$_3$): $\Lambda$6.70 (C$_5$H$_4$, d, 4H), 5.83 (C$_5$H$_4$, d, 4H), 3.85 (CH$_2$, t, 2H), 2.32 (CH$_2$H m, 2H), 1.88 (CH$_2$, m, 2H), 1.80 (CH$_3$, s, 3H, 1.45 (OH, s, 1H).

Example 5

Preparaion of Catalyst

Catalyst 1

2,2-bis(cyclopentadienyl)-5-trimethylsiloxypentane zirconium dichloride (40 mg, 0.089 mmoles) was placed in a 100 ml Schlenk flask and dissolved in toluene (50 ml). From this solution 4.3 ml (0.0077 mmol) were taken in a syringe and injected into the Büchi reactor.

Catalyst 2

TA02794/HL/PQ/3 silica-MAO provided by Witco (5.0 g) was placed in a round bottom flask under nitrogen and toluene (150 ml) was added. While mechanically stirring, a yellow solution of 2,2-bis(cyclopentadienyl)-5-trimethylsiloxypentane zirconium dichloride (161 mg, 0.359 mmol) in toluene (30 ml) was added via cannula. The orange suspension was mechanically stirred for a 2 h. period at room temperature. The slurry was filtered, washed with toluene and dried under vacuum for 16 h. The resulting catalyst was analyzed by X-Ray fluorescence: 0.59% Zr and 22.7% Al.

Catalyst 3

TA02794/HL/04 silica-MAO provided by Witco (5.2 g) was placed in a round bottom flask under nitrogen and toluene (85 ml) was added. While mechanically stirring, a yellow solution of 2,2-bis(cyclopentadienyl)-5-trimethylsiloxypentane zirconium dichloride (165 mg, 0.368 mmol) in toluene (25 ml) was added via cannula. The red suspension was mechanically stirred for a 2 h period at room temperature. The slurry was filtered, washed with toluene and dried under vacuum for 16 h. The resulting catalyst was analyzed by X-Ray fluorescence: 0.58% Zr and 20.50% Al.

Catalyst 4

2,2-bis(cyclopentadienyl)-5-hydroxypentane zirconium dichloride (5 mg, 0.013 mmol) was placed in a 25 ml Schlenk flask and dissolved in toluene (3 ml), 10 ml of MAO (0.81 M in toluene) were added and the solution was stirred for 1 h. This solution was taken in a syringe and injected into the Büchi reactor.

Catalyst 5

TA02794/HL/04 silica-MAO provided by Witco (3.0 g) was placed in a round bottom flask under nitrogen and toluene (85 ml) was added. While mechanically stirring, a yellow solution of 2,2-bis(cyclopentadienyl)-5-hydroxypentane zirconium dichloride (85 mg, 0.225 mmol) in toluene (25 ml) was added via cannula. The green suspension was mechanically stirred for a 2 h period at room temperature. The slurry was filtered, washed with toluene and dried under vacuum for 16 h. The resulting catalyst was analyzed by X-Ray fluorescence: 0.54% Zr and 22.10% Al.

Example 6

Polymerization

Experiment 1

Polymerizaon was carried out in a 1l Büchi reactor under dry conditions. The reactor was charged with 600 ml of dry heptane and heated to 90° C. Cocatalyst was added via syringe at room pressure, then it was increased to 4 bar and catalyst 1 was injected. The slurry of the forming polymer was stirred at 1200 rpm for 15 minutes. After this time, ethylene feed was closed and the reactor vented to room atmosphere. The slury was collected and stirred with acidified methanol for several hours, filtered and vacuum-dried, Activity was measured as grams of polymer per mol of catalyst per atmosphere per hour.

Experiment 2

The polymerization was carried out in the same reactor and under the same conditions than experiment 1, but in this case hexene was added right after the cocatalyst at room pressure, then it was increased to 4 bar and catalyst 1 is injected.

Experiment 3

The polymerization was carried out in the same reactor and under the same conditions than experiment 1, but in this case hexene was added right after the cocatalyst at room pressure, then it was increased to 3,75 bar and the corresponding amount of catalyst 2 was added with 0.25 bar overpressure of ethylene.

Experiment 4

The polymerization was carried out in the same reactor and under the same conditions than experiment 1, but in this case hexene was added right after the cocatalyst at room pressure, then it was increased to 3.75 bar and the corresponding amount of catalyst 2 was added with 0.25 bar overpressure of ethylene.

Experiment 5

The polymerization was carried out in the same reactor and under the same conditions than experiment 1, but in this case hexene was added right after the cocatalyst at room pressure, then it was increased to 3.75 bars and the corresponding amount of catalyst 3 was added with 0.25 bars overpressure of ethylene.

Experiment 6

The polymerization was carried out in the same reactor and under the same conditions than experiment 1, but in this case hexene was added right after the cocatalyst at room pressure, then it was increased 4 bar and catalyst 4 is injected.

Experiment 7

The polymerization was carried out in the some reactor and under the same conditions than experiment 1, but in this case hexene was added right after the cocatalyst at room pressure, then it was increased to 3.75 bars and the corresponding amount of catalyst 5 was added with 0.25 bars overpressure of ethylene.

TABLE I

Polymerization results
Table of data

| | Reaction | | Catalyst | | Cocatalyst | | | | Comonomer | Polymer | | | |
|---|---|---|---|---|---|---|---|---|---|---|---|---|---|
| Experiment | Catalyst | Type | g | Zr (mmol) | Type | Molar | mL | Al/Zr | Hexene (ml) | g | Activity | Mw | Mw/Mn |
| 1 | 1 | Homog. | 0.0035 | 0.0077 | MAO | 1.50 | 26.67 | 5000 | 0 | 4.42 | 5.74E + 05 | 37000 | 12.50 |
| 2 | 1 | Homog. | 0.0035 | 0.0077 | MAO | 1.50 | 26.67 | 5000 | 10 | 8.30 | 1.08E + 06 | 21100 | 9.72 |
| 3 | 2 | Heterog. | 0.1620 | 0.0105 | TIBA | 0.66 | 13.84 | 870 | 10 | 0.90 | 8.54E + 04 | | |
| 4 | 2 | Heterog. | 0.1020 | 0.0066 | MAO | 1.50 | 6.60 | 1500 | 10 | 4.48 | 3.39E + 05 | | |
| 5 | 3 | Heterog. | 0.2000 | 0.0138 | MAO | 1.50 | 13.80 | 1500 | 10 | 6.17 | 4.47E + 05 | 30500 | 3.32 |
| 6 | 4 | Homog. | 0.0050 | 0.0133 | MAO | 0.81 | 10.00 | 600 | 10 | 6.92 | 5.21E + 05 | 27900 | 4.64 |
| 7 | 5 | Heterog. | 0.2000 | 0.0188 | MAO | 0.81 | 17.80 | 1200 | 10 | 3.27 | 2.76E + 05 | 55900 | 12.15 |

Activity in g of polymer/mol of catalyst*atmosphere*hour
MAO methylalumoxane;
TIBA triisobutyl aluminum

What is claimed is:

1. A single-carbon bridged bis cyclopentadienyl compound having a general formula I $$\begin{array}{c} A \\ \diagdown \\ R^2 \diagdown \diagup L \\ C \\ \diagup \diagdown \\ R^2 \diagup \diagdown L; \\ A \end{array} \quad \text{I}$$

wherein
the L's are equal to or different from each other, and wherein each L is independently selected from the group consisting of:

[structures shown: substituted cyclopentadienyl, indenyl, fluorenyl, tetrahydroindenyl, octahydrofluorenyl, and benzindenyl groups, each bearing $R^1$ substituents and an H]

wherein:
the $R^1$'s are equal to or different from each other, wherein each $R^1$ independently is: hydrogen, a monovalent aliphatic hydrocarbon group, or a monovalent aliphatic aromatic hydrocarbon group, wherein each hydrocarbon group optionally contains one or more heteroatoms selected from the group consisting of group 14 through group 16 elements of the Periodic Table of the Elements and boron; and wherein optionally two $R^1$'s form an aromatic or aliphatic ring;
the $R^2$'s are equal to or different from each other, wherein each $R^2$ independently is: $C_1$–$C_{20}$ alkylidene, $C_3$–$C_{20}$ cycloalkylidene, $C_2$–$C_{20}$ alkenylidene, $C_6$–$C_{20}$ arylidene, $C_7$–$C_{20}$ alkylarylidene, $C_7$–$C_{20}$ arylalkylidene, $C_8$–$C_{20}$ arylalkenylidene, $C_8$–$C_{20}$ alkenylarylidene, wherein each $R^2$ is linear or branched, and wherein each $R^2$ optionally contains one or more heteroatoms selected from the group consisting of group 14 through group 16 elements of the Periodic Table of the Elements and boron;
one $R^2$ is optionally absent; wherein if one $R^2$ is absent, then A is directly bonded to C and is optionally hydrogen;
the A's are equal to or different from each other, and wherein each A independently is: hydrogen, $OR^3$, $NRR^4$, or $SR^5$;
wherein:
each $R^3$ independently is: R, $SiR_3$, $SO_2R$, $CR_2OR$, $CR_2SR$, or any other group used as a protective group of alcohols in organic synthesis;
each $R^4$ independently is: R, $SiR_3$, $SO_2R$, or any other group used as a protective group of amines in organic synthesis;
each $R^5$ independently is: R, $SiR_3$, $CR_2OR$, $CR_2SR$, or any other group used as a protective group of thiols in organic synthesis;
each R independently is: $C_1$–$C_{20}$ alkyl, $C_3$–$C_{20}$ cycloalkyl, $C_6$–$C_{20}$ aryl, $C_2$–$C_{20}$ alkenyl, $C_7$–$C_{20}$ arylalkyl, $C_7$–$C_{20}$ alkylaryl, $C_8$–$C_{20}$ arylalkenyl, or $C_8$–$C_{20}$ alkenylaryl, wherein each R is optionally linear or branched; and
wherein optionally two R's form an aliphatic ring or an aromatic ring;
with a proviso that at least one A is not hydrogen.

2. A bis cyclopentadienyl compound according to claim 1 wherein each $R^1$ independently is: hydrogen; $C_1$–$C_{20}$ alkyl; $C_3$–$C_{20}$ cycloalkyl; $C_6$–$C_{20}$ aryl; $C_2$–$C_{20}$ alkenyl; $C_7$–$C_{20}$ arylalkyl; $C_7$–$C_{20}$ alkylaryl; $C_8$–$C_{20}$ arylalkenyl; $C_8$–$C_{20}$ alkenylaryl; wherein each $R^1$ is optionally linear or branched, and wherein each $R^1$ is optionally substituted by $BR_2$, OR, $SiR_3$, or $NR_2$.

3. A bis cyclopentadienyl compound according to claim 1, wherein each R independently is: butyl, propyl, ethyl, or methyl.

4. A bis cyclopentadienyl compound according to claim 1, wherein each $R^2$ independently is: butylidene, propylidene, ethylidene, or methylene.

5. A bis cyclopentadienyl compound according to claim 1, wherein at least one A is $OSiR_3$.

6. A process for obtaining a bis cyclopentadienyl compound as claimed in claim 1, the process comprising:
contacting a metallating compound selected from the group consisting of: organolithium compounds, organosodium compounds, organopotassium compounds, organomagnesium, sodium hydride, potassium hydride, lithium, sodium, and potassium with an LH compound selected from the group consisting of:

[structures shown]

-continued

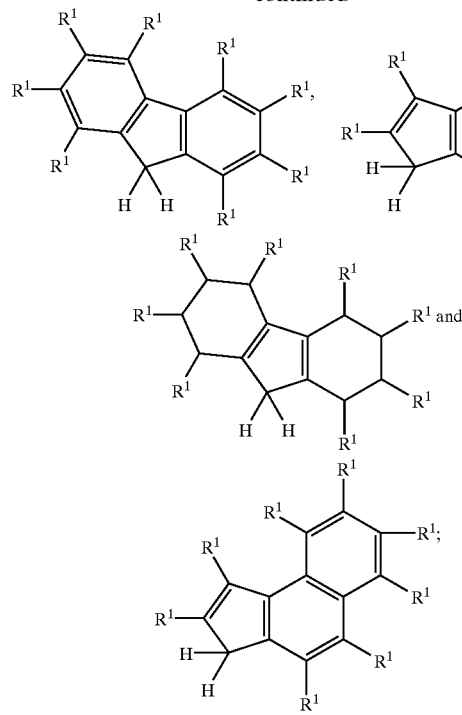

and with a compound of a general formula II

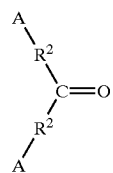

to yield a product having a temperature;
increasing the temperature of the product; and recovering the product.

7. A process for preparing a bis cyclopentadienyl compound as claimed in claim 1 wherein the two L groups are different from each other, the process comprising:
contacting a metallating compound selected from the group consisting of: organolithium compounds, organosodium compounds, organopotassium compounds, organomagnesium, sodium hydride, potassium hydride, lithium, sodium, and potassium with a first LH compound selected from the group consisting of:

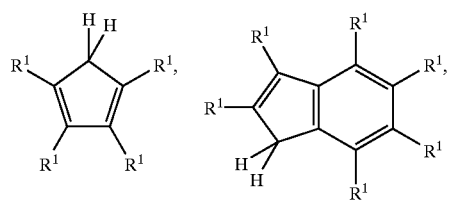

-continued

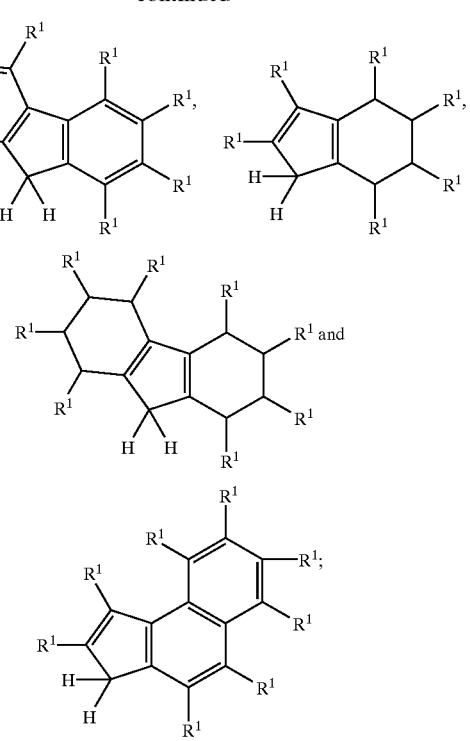

and with a compound of a general formula II

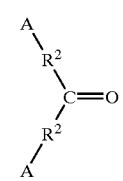

to yield a reaction mixture;
adding a second LH compound different from the first LH compound, wherein the second LH compound is selected from the group consisting of

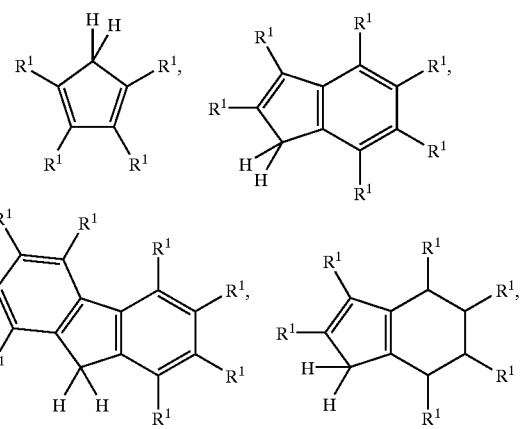

-continued

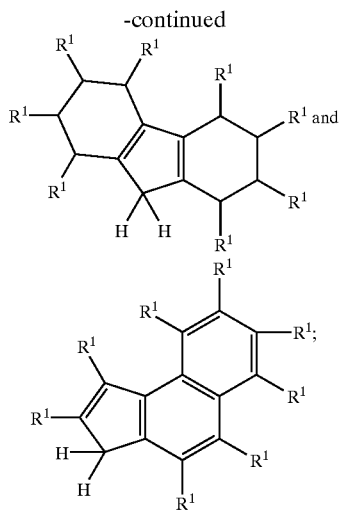

adding a second amount of the metallating compound to yield a product having a temperature;

increasing the temperature of the product; and then recovering the product.

8. A process according to claim 7, wherein the steps of adding the second LH compound and adding the second amount of the metallating compound comprise premixing the second LH compound with the second amount of the metallating compound to yield a compound mixture, and then adding the compound mixture to the reaction mixture.

9. A metallocene complex having a formula III

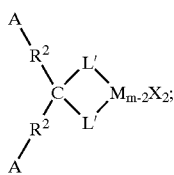

III wherein:

each L' is independently a cyclopentadienyl compound which forms with a metal an $\eta^5$ complex, and is selected from the group consisting of:

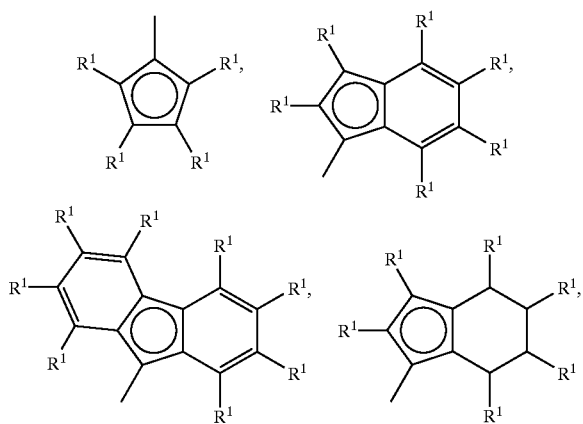

-continued

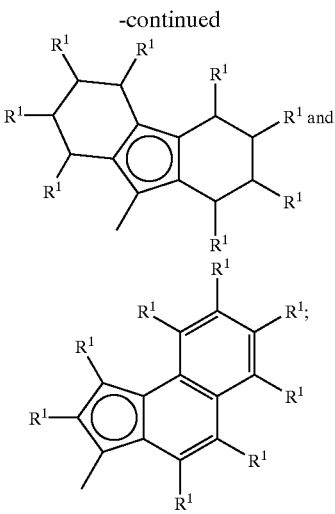

M is a transition metal selected from the group consisting of group 3 through group 6 elements of the Periodic Table of the Elements; m is a number coinciding with an oxidation state of the transition metal;

the X's are equal to or different from each other, wherein each X independently is selected from the group consisting of: halogen, hydrogen, OR, $N(R)_2$, $C_1$–$C_{20}$ alkyl, and $C_6$–$C_{20}$ aryl.

10. A metallocene complex according to claim 9 wherein M is: zirconium, titanium, or hafnium; and wherein X is halogen.

11. A process for obtaining a metallocene complex as claimed in claim 9, the process comprising the following steps:

a) reacting a bis cyclopentadienyl compound having a general formula I with a metallating compound selected from the group consisting of: organolithium compounds, organosodium compounds, organopotassium compounds, organomagnesium, sodium hydride, potassium hydride, lithium, sodium, and potassium to yield an obtained product; and b) reacting the obtained product with a compound of general formula $MX_mE_q$, wherein E is an ether or an amine forming an adduct with M and q is 0, 1, 2, 3, or 4.

12. A metallocene complex having a general formula IV

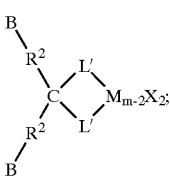

IV wherein each B is selected from the group consisting of: OH, NRH, and SH.

13. A catalyst for polymerization of olefins comprising at least a metallocene complex according to claim 9 and a cocatalyst.

14. A polymerization catalyst according to claim 13 further comprising an inorganic support.

15. A supported polymerization catalyst according to claim 14 wherein the inorganic support is selected from the group consisting of: silica, MAO modified silica, alumina, silica alumina, aluminum phosphates, and mixtures thereof.

16. A supported polymerization catalyst according to claim 14, wherein at least one group A of the metallocene complex is OSiR₃ and the inorganic support is MAO modified silica.

17. A process for obtaining a polymerization catalyst according to claim 14, the process comprising the following steps:
   a) reacting, under anhydrous conditions and an inert atmosphere, a solution of at least one metallocene complex of formula III or IV with a suspension of the inorganic support in an aliphatic or aromatic hydrocarbon at a temperature between −20° C. and 90° C. to yield a product; and
   b) filtering and washing the product with an aliphatic or aromatic hydrocarbon.

18. A process for preparing a polymer, the process comprising polymerizing an olefin monomer by contacting the olefin monomer with the catalyst claimed in claim 13 to yield the polymer.

19. A single-carbon bridged bis cyclopentadienyl compound as claimed in claim 1, wherein the single-carbon bridged bis cyclopentadienyl compound is selected from the group consisting of:
1-trimethylsiloxy-4,4-bis(cyclopentadienyl)pentane;
1-trimethylsiloxy-4,4-bis(indenyl)pentane;
1-trimethylsiloxy-4,4-bis(fluorenyl)pentane;
1-trimethylsiloxy-4,4-bis(tetrahydroindenyl)pentane;
1-trimethylsiloxy-4,4-bis(octahydrofluorenyl)pentane;
1,5-bis-trimethylsiloxy-4,4-bis(cyclopentadienyl)pentane;
1,5-bis-trimethylsiloxy-4,4-bis(indenyl)pentane;
1,5-bis-trimethylsiloxy-4,4-bis(fluorenyl)pentane;
1,5-bis-trimethylsiloxy-4,4-bis(tetrahydroindenyl)pentane;
1,5-bis-trimethylsiloxy-4,4-bis(octahydrofluorenyl)pentane;
1-trimethylsiloxy-4-cyclopentadienyl-4-indenyl-pentane;
1-trimethylsiloxy-4-cyclopentadienyl-4-fluorenyl-pentane;
1-trimethylsiloxy-4-cyclopentadienyl-4-tetrahydroindenyl-pentane;
1-trimethylsiloxy-4-cyclopentadienyl-4-octahydrofluorenyl-pentane;
1-trimethylsiloxy-3,3-bis(cyclopentadienyl)pentane;
1-trimethylsiloxy-3,3-bis(indenyl)pentane;
1-trimethylsiloxy-3,3-bis(fluorenyl)pentane;
1-trimethylsiloxy-3,3-bis(tetrahydroindenyl)pentane;
1-trimethylsiloxy-3,3-bis(octahydrofluorenyl)pentane;
1,5-bis-trimethylsiloxy-3,3-bis(cyclopentadienyl)pentane;
1,5-bis-trimethylsiloxy-3,3-bis(indenyl)pentane;
1,5-bis-trimethylsiloxy-3,3-bis(fluorenyl)pentane;
1,5-bis-trimethylsiloxy-3,3-bis(tetrahydroindenyl)pentane;
1,5-bis-trimethylsiloxy-3,3-bis(octahydrofluorenyl)pentane;
1-trimethylsiloxy-3-cyclopentadienyl-3-indenyl-pentane;
1-trimethylsiloxy-3-cyclopentadienyl-3-fluorenyl-pentane;
1-trimethylsiloxy-3-cyclopentadienyl-3-tetrahydroindenyl-pentane;
1-trimethylsiloxy-3-cyclopentadienyl-3-octahydrofluorenyl-pentane;
1-triethylsiloxy-4,4-bis(cyclopentadienyl)pentane;
1-triethylsiloxy-4,4-bis(indenyl)pentane;
1-triethylsiloxy-4,4-bis(fluorenyl)pentane;
1-triethylsiloxy-4,4-bis(tetrahydroindenyl)pentane;
1-triethylsiloxy-4,4-bis(octahydrofluorenyl)pentane;
1,5-bis-triethylsiloxy-4,4-bis(cyclopentadienyl)pentane;
1,5-bis-triethylsiloxy-4,4-bis(indenyl)pentane;
1,5-bis-triethylsiloxy-4,4-bis(fluorenyl)pentane;
1,5-bis-triethylsiloxy-4,4-bis(tetrahydroindenyl)pentane;
1,5-bis-triethylsiloxy-4,4-bis(octahydrofluorenyl)pentane;
1-triethylsiloxy-4-cyclopentadienyl-4-indenyl-pentane;
1-triethylsiloxy-4-cyclopentadienyl-4-fluorenyl-pentane;
1-triethylsiloxy-4-cyclopentadienyl-4-tetrahydroindenyl-pentane;
1-triethylsiloxy-4-cyclopentadienyl-4-octahydrofluorenyl-pentane;
1-triethylsiloxy-3,3-bis(cyclopentadienyl)pentane,
1-triethylsiloxy-3,3-bis(indenylpenyl)pentane;
1-triethylsiloxy-3,3-bis(fluorenyl)pentane;
1-triethylsiloxy-3,3-bis(tetrahydroindenyl)pentane;
1-triethylsiloxy-3,3-bis(octahydrofluorenyl)pentane;
1,5-bis-triethylsiloxy-3,3-bis(cyclopentadienyl)pentane;
1,5-bis-triethylsiloxy-3,3-bis(indenyl)pentane;
1,5-bis-triethylsiloxy-3,3-bis(fluorenyl)pentane;
1,5-bis-triethylsiloxy-3,3-bis(tetrahydroindenyl)pentane;
1,5-bis-triethylsiloxy-3,3-bis(octahydrofluorenyl)pentane;
1-triethylsiloxy-3-cyclopentadienyl-3-indenyl-pentane;
1-triethylsiloxy-3-cyclopentadienyl-3-fluorenyl-pentane;
1-triethylsiloxy-3-cyclopentadienyl-3-tetrahydroindenyl-pentane;
1-triethylsiloxy-3-cyclopentadienyl-3-octahydrofluorenyl-pentane;
1-triphenylsiloxy-4,4-bis(cyclopentadienyl)pentane;
1-triphenylsiloxy-4,4-bis(indenyl)pentane;
1-triphenylsiloxy-4,4-bis(fluorenyl)pentane;
1-triphenylsiloxy-4,4-bis(tetrahydroindenyl)pentane;
1-triphenylsiloxy-4,4-bis(octahydrofluorenyl)pentane;
1,5-bis-triphenylsiloxy-4,4-bis(cyclopentadienyl)pentane;
1,5-bis-triphenylsiloxy-4,4-bis(indenyl)pentane;
1,5-bis-triphenylsiloxy-4,4-bis(fluorenyl)pentane;
1,5-bis-triphenylsiloxy-4,4-bis(tetrahydroindenyl)pentane;
1,5-bis-triphenylsiloxy-4,4-bis(octahydrofluorenyl)pentane;
1-triphenylsiloxy-4-cyclopentadienyl-4-indenyl-pentane;
1-triphenylsiloxy-4-cyclopentadienyl-4-fluorenyl-pentane;
1-triphenylsiloxy-4-cyclopentadienyl-4-tetrahydroindenyl-pentane;
1-triphenylsiloxy-4-cyclopentadienyl-4-octahydrofluorenyl-pentane;
1-triphenylsiloxy-3,3-bis(cyclopentadienyl)pentane;
1-triphenylsiloxy-3,3-bis(indenyl)pentane;
1-triphenylsiloxy-3,3-bis(fluorenyl)pentane;
1-triphenylsiloxy-3,3-bis(tetrahydroindenyl)pentane;
1-triphenylsiloxy-3,3-bis(octahydrofluorenyl)pentane;
1,5-bis-triphenylsilyl-3,3-bis(cyclopentadienyl)pentane;
1,5-bis-triphenylsiloxy-3,3-bis(indenyl)pentane;
1,5-bis-triphenylsiloxy-3,3-bis(fluorenyl)pentane;
1,5-bis-triphenylsiloxy-3,3-bis(tetrahydroindenyl)pentane;
1,5-bis-triphenylsiloxy-3,3-bis(octahydrofluorenyl)pentane;
1-triphenylsiloxy-3-cyclopentadienyl-3-indenyl-pentane;
1-triphenylsiloxy-3-cyclopentadienyl-3-fluorenyl-pentane;
1-triphenylsiloxy-3-cyclopentadienyl-3-tetrahydroindenyl-pentane; and
1-triphenylsiloxy-3-cyclopentadienyl-3-octahydrofluorenyl-pentane.

20. A process as claimed in claim 6, wherein the compound of general formula II is selected from the group consisting of:
1-trimethylsiloxy-pentane-2-one;
1-trimethylsiloxy-pentane-3-one;
1-trimethylsiloxy-pentane-4-one;
1,5-bis-trimethylsiloxy-pentane-3-one;
1-trimethylsiloxy-hexane-5-one;
1-trimethylsiloxy-hexane-4-one;
1-trimethylsiloxy-hexane-3-one;
1-trimethylsiloxy-hexane-2-one;
1,6bis-trimethylsiloxy-hexane-3-one;
1-trimethylsiloxy-heptane-6-one;
1-trimethylsiloxy-heptane-5-one;
1-trimethylsiloxy-heptane-4-one;

1-trimethylsiloxy-heptane-3-one;
1-trimethylsiloxy-heptane-2-one;
1,7-bis-trimethylsiloxy-heptane-4-one;
1-triethylsiloxy-pentane-2-one;
1-triethylsiloxy-pentane-3one;
1-triethylsiloxy-pentane-4-one;
1,5-bis-triethylsiloxy-pentane-3-one;
1-triethylsiloxy-hexane-5-one;
1-triethylsiloxy-hexane-4-one;
1-triethylsiloxy-hexane-3-one;
1-triethylsiloxy-hexane-2-one;
1,6-bis-triethylsiloxy-hexane-3-one;
1-triethylsiloxy-heptane-6-one;
1-triethylsiloxy-heptane-5-one;
1-triethylsiloxy-heptane-4-one;
1-triethylsiloxy-heptane-3-one;
1-triethylsiloxy-heptane-2-one;
1,7-bis-triethylsiloxy-heptane-4-one;
1-triphenylsiloxy-pentane-2-one;
1-triphenylsiloxy-pentane-3-one;
1-triphenylsiloxy-pentane-4-one;
1,5-bis-triphenylsiloxy-pentane-3-one;
1-triphenylsiloxy-hexane-5-one;
1-triphenylsiloxy-hexane-4-one;
1-triphenylsiloxy-hexane-3-one;
1-triphenylsiloxy-hexane-2-one;
1,6-bis-triphenylsiloxy-hexane-3-one;
1-triphenylsiloxy-heptane-6-one;
1-triphenylsiloxy-heptane-5-one;
1-triphenylsiloxy-heptane-4-one;
1-triphenylsiloxy-heptane-3-one;
1-triphenylsiloxy-heptane-2-one; and
1,7-bis-1-triphenylsiloxy-heptane-4-one.

21. A metallocene complex as claimed in claim 9, wherein the metallocene complex is selected from the group consisting of:
(1-trimethylsiloxy-4,4-bis(cyclopentadienyl)pentane) zirconium dichloride;
(1-trimethylsiloxy-4,4-bis(indenyl)pentane)zirconium dichloride;
(1-trimethylsiloxy-4,4-bis(fluoreny)pentane)zirconium dichloride;
(1-trimethylsiloxy-4,4-bis(tetrahydroindenyl)pentane) zirconium dichloride;
(1-trimethylsiloxy-4,4-bis(octahydrofluorenyl)pentane) zirconium dichloride;
(1,5-bis-trimethylsiloxy-4,4-bis(cyclopentadienyl)pentane) zirconium dichloride;
(1,5-bis-trimethylsiloxy-4,4-bis(indenyl)pentane)zirconium dichloride;
(1,5-bis-trimethylsiloxy-4,4-bis(fluorenyl)pentane) zirconium dichloride;
(1,5-bis-trimethylsiloxy-4,4-bis(tetrahydroindenyl)pentane) zirconium dichloride;
(1,5-bis-trimethylsiloxy-4,4-bis(octahydrofluorenyl) pentane)zirconium dichloride;
(1-trimethylsiloxy-4-cyclopentadienyl-4-indenyl-pentane) zirconium dichloride;
(1-trimethylsiloxy-4-cyclopentadienyl-4-fluorenyl-pentane) zirconium dichloride;
(1-trimethylsiloxy-4-cyclopentadienyl-4-tetrahydroindenyl-pentane)zirconium dichloride;
(1-trimethylsiloxy-4-cyclopentadienyl-4-octahydrofluorenyl-pentane)zirconium dichloride;
(1-trimethylsiloxy-3,3-bis(cyclopentadienyl)pentane) zirconium dichloride;
(1-trimethylsiloxy-3,3-bis(indenyl)pentane)zirconium dichloride;
(1-trimethylsiloxy-3,3-bis(fluorenyl)pentane)zirconium dichloride;
(1-trimethylsiloxy-3,3-bis(tetrahydroindenyl)pentane) zirconium dichloride;
(1-trimethylsiloxy-3,3-bis(octahydrofluorenyl)pentane) zirconium dichloride;
(1,5-bis-trimethylsiloxy-3,3-bis(cyclopentadienyl)pentane) zirconium dichloride;
(1,5-bis-trimethylsiloxy-3,3-bis(indenyl)pentane)zirconium dichloride;
(1,5-bis-trimethylsiloxy-3,3-bis(fluorenyl)pentane) zirconium dichloride;
(1,5-bis-trimethylsiloxy-3,3-bis(tetrahydroindenyl)pentane) zirconium dichloride;
(1,5-bis-trimethylsiloxy-3,3-bis(octahydrofluorenyl) pentane)zirconium dichloride;
(1-trimethylsiloxy-3-cyclopentadienyl-3-indenyl-pentane) zirconium dichloride;
(1-trimethylsiloxy-3-cyclopentadienyl-3-fluorenyl-pentane) zirconium dichloride;
(1-trimethylsiloxy-3-cyclopentadienyl-3-tetrahydroindenyl-pentane)zirconium dichloride;
(1-trimethylsiloxy-3-cyclopentadienyl-3-octahydrofluorenyl-pentane)zirconium dichloride;
(1-triethylsiloxy-4,4-bis(cyclopentadienyl)pentane) zirconium dichloride;
(1-triethylsiloxy-4,4-bis(indenyl)pentane)zirconium dichloride;
(1-triethylsiloxy-4,4-bis(fluorenyl)pentane)zirconium dichloride;
(1-triethylsiloxy-4,4-bis(tetrahydroindenyl)pentane) zirconium dichloride;
(1-triethylsiloxy-4,4-bis(octahydrofluorenyl)pentane) zirconium dichloride;
(1,5-bis-triethylsiloxy-4,4-bis(cyclopentadienyl)pentane) zirconium dichloride;
(1,5-bis-triethylsiloxy-4,4-bis(indenyl)pentane) zirconium dichloride;
(1,5-bis-triethylsiloxy-4,4-bis(fluorenyl)pentane) zirconium dichloride;
(1,5-bis-triethylsiloxy-4,4-bis(tetrahydroindenyl)pentane) zirconium dichloride;
(1,5-bis-triethylsiloxy4,4-bis(octahydrofluorenyl)pentane) zirconium dichloride;
(1-triethylsiloxy-4-cyclopentadienyl-4-indenyl-pentane) zirconium dichloride;
(1-triethylsiloxy-4-cyclopentadienyl-4-fluorenyl-pentane) zirconium dichloride;
(1-triethylsiloxy-4-cyclopentadienyl-4-tetrahydroindenyl-pentane)zirconium dichloride;
(1-triethylsiloxy-4-cyclopentadienyl-4-octahydrofluorenyl-pentane)zirconium dichloride;
(1-triethylsiloxy-3,3-bis(cyclopentadienyl)pentane) zirconium dichloride;
(1-triethylsiloxy-3,3-bis(indenyl)pentane)zirconium dichloride;
(1-triethylsiloxy-3,3-bis(fluorenyl)pentane)zirconium dichloride;
(1-triethylsiloxy-3,3-bis(tetrahydroindenyl)pentane) zirconium dichloride;
(1-triethylsiloxy-3,3-bis(octahydrofluorenyl)pentane) zirconium dichloride;
(1,5-bis-triethylsiloxy-3,3-bis(cyclopentadienyl)pentane) zirconium dichloride;
(1,5-bis-triethylsiloxy-3,3-bis(indenyl)pentane)zirconium dichloride;
(1,5-bis-triethylsiloxy-3,3-bis(fluorenyl)pentane)zirconium dichloride;

(1,5-bis-triethylsiloxy-3,3-bis(tetrahydroindenyl)pentane) zirconium dichloride;
(1,5-bis-triethylsiloxy-3,3-bis(octahydrofluorenyl)pentane) zirconium dichloride;
(1-triethylsiloxy-3-cyclopentadienyl-3-indenyl-pentane) zirconium dichloride;
(1-triethylsiloxy-3-cyclopentadienyl-3-fluorenyl-pentane) zirconium dichloride;
(1-triethylsiloxy-3-cyclopentadienyl-3-tetrahydroindenyl-pentane)zirconium dichloride;
(1-triethylsiloxy-3-cyclopentadienyl-3-octahydrofluorenyl-pentane) zirconium dichloride;
(1-triphenylsiloxy-4,4-bis(cyclopentadienyl)pentane) zirconium dichloride;
(1-triphenylsiloxy-4,4-bis(indenyl)pentane)zirconium dichloride;
(1-triphenylsiloxy-4,4-bis(fluorenyl)pentane)zirconium dichloride;
(1-triphenylsiloxy-4,4-bis(tetrahydroindenyl)pentane) zirconium dichloride;
(1-triphenylsiloxy-4,4-bis(octahydrofluorenyl)pentane) zirconium dichloride;
(1,5-bis-triphenylsiloxy-4,4-bis(cyclopentadienyl)pentane) zirconium dichloride;
(1,5-bis-triphenylsiloxy-4,4-bis(indenyl)pentane)zirconium dichloride;
(1,5-bis-triphenylsiloxy-4,4-bis(fluorenyl)pentane) zirconium dichloride;
(1,5-bis-triphenylsiloxy-4,4-bis(tetrahydroindenyl)pentane) zirconium dichloride;
(1,5-bis-triphenylsiloxy-4,4-bis(octahydrofluorenyl) pentane)zirconium dichloride;
(1-triphenylsiloxy-4-cyclopentadienyl-4-indenyl-pentane) zirconium dichloride;
(1-triphenylsiloxy-4-cyclopentadienyl-4-fluorenyl-pentane) zirconium dichloride;
(1-triphenylsiloxy-4-cyclopentadienyl-4-tetrahydroindenyl-pentane)zirconium dichloride;
(1-triphenylsiloxy-4-cyclopentadienyl-4-octahydrofluorenyl-pentane)zirconium dichloride;
(1-triphenylsiloxy-3,3-bis(cyclopentadienyl)pentane) zirconium dichloride;
(1-triphenylsiloxy-3,3-bis(indenyl)pentane)zirconium dichloride;
(1-triphenylsiloxy-3,3-bis(fluorenyl)pentane)zirconium dichloride;
(1-triphenylsiloxy-3,3-bis(tetrahydroindenyl)pentane) zirconium dichloride;
(1-triphenylsiloxy-3,3-bis(octahydrofluorenyl)pentane) zirconium dichloride;
(1,5-bis-triphenylsiloxy-3,3-bis(cyclopentadienyl)pentane) zirconium dichloride;
(1,5-bis-triphenylsiloxy-3,3-bis(indenyl)pentane)zirconium dichloride;
(1,5-bis-triphenylsiloxy-3,3-bis(fluorenyl)pentane) zirconium dichloride;
(1,5-bis-triphenylsiloxy-3,3-bis(tetrahydroindenyl)pentane) zirconium dichloride;
(1,5-bis-triphenylsiloxy-3,3-bis(octahydrofluorenyl) pentane)zirconium dichloride;
(1-triphenylsiloxy-3-cyclopentadienyl-3-indenyl-pentane) zirconium dichloride;
(1-triphenylsiloxy-3-cyclopentadienyl-3-fluorenyl-pentane) zirconium dichloride;
(1-triphenylsiloxy-3-cyclopentadienyl-3-tetrahydroindenyl-pentane)zirconium dichloride; and
(1-triphenylsiloxy-3-cyclopentadienyl-3-octahydrofluorenyl-pentane)zirconium dichloride.

22. A metallocene complex as claimed in claim 12, wherein the metallocene complex is selected from the group consisting of:
(1-hydroxy-4,4-bis(cyclopentadienyl)pentane)zirconium dichloride;
(1-hydroxy-4,4-bis(indenyl)pentane)zirconium dichloride;
(1-hydroxy-4,4-bis(fluorenyl)pentane)zirconium dichloride;
(1-hydroxy-4,4-bis(tetrahydroindenyl)pentane)zirconium dichloride;
(1-hydroxy-4,4-bis(octahydrofluorenyl)pentane)zirconium dichloride;
(1,5-bis-hydroxy-4,4-bis(cyclopentadienyl)pentane) zirconium dichloride;
(1,5-bis-hydroxy-4,4-bis(indenyl)pentane)zirconium dichloride;
(1,5-bis-hydroxy-4,4-bis(fluorenyl)pentane)zirconium dichloride;
(1,5-bis-hydroxy-4,4-bis(tetrahydroindenyl)pentane) zirconium dichloride;
(1,5-bis-hydroxy-4,4-bis(octahydrofluorenyl)pentane) zirconium dichloride;
(1-hydroxy-4-cyclopentadienyl-4-indenyl-pentane) zirconium dichloride;
(1-hydroxy-4-cyclopentadienyl-4-fluorenyl-pentane) zirconium dichloride;
(1-hydroxy-4-cyclopentadienyl-4-tetrahydroindenyl-pentane)zirconium dichloride;
(1-hydroxy-4-cyclopentadienyl-4-octahydrofluorenyl-pentane)zirconium dichloride;
(1-hydroxy-3,3-bis(cyclopentadienyl)pentane)zirconium dichloride;
(1-hydroxy-3,3-bis(indenyl)pentane)zirconium dichloride;
(1-hydroxy-3,3-bis(fluorenyl)pentane)zirconium dichloride;
(1-hydroxy-3,3-bis(tetrahydroindenyl)pentane)zirconium dichloride;
(1-hydroxy-3,3-bis(octahydrofluorenyl)pentane)zirconium dichloride;
(1,5-bis-hydroxy-3,3-bis(cyclopentadienyl)pentane) zirconium dichloride;
(1,5-bis-hydroxy-3,3-bis(indenyl)pentane)zirconium dichloride;
(1,5-bis-hydroxy-3,3-bis(fluorenyl)pentane)zirconium dichloride;
(1,5-bis-hydroxy-3,3-bis(tetrahydroindenyl)pentane) zirconium dichloride;
(1,5-bis-hydroxy-3,3-bis(octahydrofluorenyl)pentane) zirconium dichloride;
(1-hydroxy-3yclopentadienyl-3-indenyl-pentane)zirconium dichloride;
(1-hydroxy-3-cyclopentadienyl-3-fluorenyl-pentane) zirconium dichloride;
(1-hydroxy-3-cyclopentadienyl-3-tetrahydroindenyl-pentane)zirconium dichloride; and
(1-hydroxy-3-cyclopentadienyl-3-octahydrofluorenyl-pentane)zirconium dichloride.

23. A process as claimed in claim 7, wherein the compound of general formula II is selected from the group consisting of:
1-trimethylsiloxy-pentane-2-one;
1-trimethylsiloxy-pentane-3-one;
1-trimethylsiloxy-pentane-4-one;
1,5-bis-trimethylsiloxy-pentane-3-one;
1-trimethylsiloxy-hexane-5-one;
1-trimethylsiloxy-hexane-4-one;
1-trimethylsiloxy-hexane-3-one;
1-trimethylsiloxy-hexane-2-one;
1,6-bis-trimethylsiloxy-hexane-3-one;

1-trimethylsiloxy-heptane-6-one;
1-trimethylsiloxy-heptane-5-one;
1-trimethylsiloxy-heptane-4-one;
1-trimethylsiloxy-heptane-3-one;
1-trimethylsiloxy-heptane-2-one;
1,7-bis-trimethylsiloxy-heptane-4-one;
1-triethylsiloxy-pentane-2-one;
1-triethylsiloxy-pentane-3-one;
1-triethylsiloxy-pentane-4-one;
1,5-bis-triethylsiloxy-pentane-3-one;
1-triethylsiloxy-hexane-5-one;
1-triethylsiloxy-hexane-4-one;
1-triethylsiloxy-hexane-3-one;
1-triethylsiloxy-hexane-2-one;
1,6-bis-triethylsiloxy-hexane-3-one;
1-triethylsiloxy-heptane-6-one;
1-triethylsiloxy-heptane-5-one;
1-triethylsiloxy-heptane-4-one;
1-triethylsiloxy-heptane-3-one;
1-triethylsiloxy-heptane-2-one;
1,7-bis-triethylsiloxy-heptane-4-one;
1-triphenylsiloxy-pentane-2-one;
1-triphenylsiloxy-pentane-3-one;
1-triphenylsiloxy-pentane-4-one;
1,5-bis-triphenylsiloxy-pentane-3-one; and
1-triphenylsiloxy-hexane-5-one.

24. A process for preparing a copolymer, the process comprising copolymerizing an olefin monomer and a comonomer by contacting the olefin monomer and the comonomer with the catalyst claimed in claim 13 to yield the copolymer.

* * * * *